United States Patent [19]

Shlyankevich

[11] Patent Number: 5,424,331

[45] Date of Patent: Jun. 13, 1995

US005424331A

[54] PHARMACEUTICAL COMPOSITIONS AND DIETARY SOYBEAN FOOD PRODUCTS FOR THE PREVENTION OF OSTEOPOROSIS

[75] Inventor: Mark Shlyankevich, Waterbury, Conn.

[73] Assignee: Bio-Virus Research Incorporated, San Matteo, Calif.

[21] Appl. No.: 258,460

[22] Filed: Jun. 10, 1994

[51] Int. Cl.⁶ ............................................ A61K 31/35
[52] U.S. Cl. .................................... 514/456; 514/874; 514/455
[58] Field of Search ........................ 514/456, 455, 874

[56] References Cited

U.S. PATENT DOCUMENTS

| | | | |
|---|---|---|---|
| 3,864,362 | 2/1975 | Feuer et al. | 260/345.2 |
| 4,501,754 | 2/1985 | Wechter et al. | 514/456 |
| 4,960,908 | 10/1990 | Ito et al. | 549/403 |

OTHER PUBLICATIONS

Endocrinology 122:5 (1988) p. 1847.
Journal of Clinical Endocrinology and Metabolism 60:6 (1988) p. 140.
First International Symposium on the Role of Soy in Preventing & Treat Chronic Disease, p. 1-27, Feb./-20-23, 1994.
Soy Intake and Cancer Risk:Review of in Vitro & in Vivo Data: Messina, Persky, Setchell and Barnes (3 pages) Nutrition and Cancer, 1994 (p. 113).
Flavonoids:Biochemical Effects & Therapeutic Applications; Brandi, pp. s3, s7, s8 *Bone and Mineral,* 19 (5 pages) 1992.
New England Journal of Medicine, 14 Apr. 1994, Effects of Vitamin E & Beta Carotene on Incidence of Lung Cancer . . . , (2 pages).
Food & Nutrition Board, National Academy of Sciences, National Research Council, Recommended Dietary Allowances, p. 451 Nutrition Reviews, vol. 50 (1992).

*Primary Examiner*—Gary E. Hollinden
*Assistant Examiner*—Brian M. Burn
*Attorney, Agent, or Firm*—Herbert Dubno; Johnathan Myers

[57] ABSTRACT

A composition for the treatment or prevention of osteoporosis, is disclosed, which comprises:

(a) 75 to 200 parts of one or more phytoestrogen compounds;
(b) 0 to 100 parts of dried licorice root extract;
(c) 300 to 600 parts of calcium contained in a biologically acceptable calcium salt;
(d) 70 to 280 parts of magnesium contained in a biologically acceptable magnesium salt;
(e) 4 to 25 parts of zinc contained in a biologically acceptable zinc salt;
(f) 5 to 20 parts of beta-carotene;
(g) 0.005 to 0.010 parts of Vitamin D as cholecalciferol; and
(h) 6 to 12 parts of Vitamin E, in admixture with a biologically acceptable inert carrier. The new compositions are administered to a mammalian subject as either a pharmaceutical or as a dietary supplement.

10 Claims, No Drawings

PHARMACEUTICAL COMPOSITIONS AND DIETARY SOYBEAN FOOD PRODUCTS FOR THE PREVENTION OF OSTEOPOROSIS

FIELD OF THE INVENTION

This invention relates to new pharmaceutical compositions and dietary soybean food products for the prevention of osteoporosis. More particularly, the invention relates to such pharmaceutical compositions and dietary soybean food products that contain natural phytoestrogens of the isoflavone or coumestan groups.

BACKGROUND OF THE INVENTION

Osteoporosis is recognized as a major public health problem in Western countries, especially among elderly white women. See Cummings, S. R. et al, Epidemiol. Rev., 7:178 to 208 (1985). Postmenopausal osteoporotic fractures affect 1.5 million people each year. About 300,000 new cases of osteoporotic hip, 650,000 of vertebrae, and 200,000 of distal forearm fractures are reported annually in the USA. Mortality in the first year after hip fractures reaches 20%. See Cooper, C. et al, Amer. J. Epidem., 1001 to 1005 (1993) and Riggs, B. L., West. J. Med., 154:63 to 67 (1991). The estimated direct cost for treatment of these patients in the USA exceeds $6 to $10 billion annually. See Holbrook, T. L. et al, Lancet, 2:1046 to 1049 (1988) and the Riggs, B. L. reference cited above. Half of the survivors are unable to walk unassisted and 25% are confined to long term care in a nursing home.

Epidemiological and clinical observations strongly indicate that osteoporosis and fractures are related to aging. See once again Cummings, S. R. et al, Epidemiol. Rev., 7:178 to 208 (1985) and also Cummings, S. R. et al, Arch. Intern. Med., 149:2445 to 2448 (1989) and Ross, P. D. et al, Am. J. Epidem., 133:801 to 809 (1991). Particularly rapid loss of bone mass is noted in the first decade after menopause, and implicates estrogen deficiency as an etiological factor.

One of the first observations by Albright more than 50 years ago noted that 40 out of 42 patients with osteoporotic fractures were postmenopausal women. See Albright, F. et al, J.Am.Med.Ass., 116:2465 to 2474 (1941). Indeed the incidence rate of hip fractures rises dramatically with age after 50, and increases about 3 times after 80; see once again Cummings, S. R. et al, Epidemiol. Rev., 7:178 to 208 (1985). It is estimated that adult white women who, on average, will live to age 80 have a 15% lifetime risk of suffering a hip fracture, but in contrast, a white man who has a 75-year life expectancy has only a 5% lifetime chance of a hip fracture. The incidence of limb fractures rises with age, from approximately 7.3 per thousand to about 40 per thousand at ages 45 and 85, respectively. See Henert, A. M. et al, Am. J. Epidem. 132:123 to 135 (1990).

Prevention is likely to remain the most effective method of dealing with osteoporosis. Estrogens can protect the patient against osteoporosis. Hormone replacement therapy starting shortly after menopause prevents rapid bone loss and leads to reduction in the fracture risk of up to 60%. Unfortunately there are side effects and other risk factors associated with using estrogens in hormone replacement to prevent postmenopausal osteoporosis.

Weak non-steroidal synthetic estrogens, tamoxifen, toremifene, etc., that are used for breast cancer therapy, have a beneficial effect on bone formation. None of these compounds, however, has proven to be satisfactory in treating osteoporosis.

Diet has also been considered in the control of osteoporosis. Most diet recommendations for the prevention or control of osteoporosis center on increasing the intake of calcium, magnesium, Vitamin D, fluorides, and restriction of the amount of salt, caffeine, alcohol, and consumed animal protein. It is known in the traditional Japanese diet that the average intake of soy products for women amounts to more than 55 g/day. Several studies have indicated that the incidence of hip fracture in Japan is considerably lower than in Western countries. In Hawaii, hip fracture rates among persons of Japanese ancestry were approximately half that of Caucasians.

It is well known that the diet in Japan includes intake of large amounts of soy products. According to The Lancet, Vol. 339, p. 1233 (16 May 1992), H. Adlercreutz et al, Dietary Phytoestrogens and the Menopause in Japan, the diet high in soy may be the reason why menopausal symptoms are much less frequent in Japan than in Western countries. The Lancet reported that the urine of several Japanese men, women, and children was analyzed and the urine was found to contain a high amount of phytoestrogens. There is no mention or suggestion in this reference, however, of specifically avoiding osteoporosis thanks to a high soy diet.

The phytoestrogens are diphenolic plant compounds that are somewhat related structurally to the mammalian sex hormone: 17-beta-estradiol. See Setchell, K. D. R., et al Am. J. Clin. Nutr., 40:569 to 578 (1984). Two chemical classes of phytoestrogens are abundant in soybeans, total soy products, and soy protein isolates. Those two classes are coumestrol and isoflavones. The latter class includes daidzein, genistein, glycitein, as well as their glycoside and acetylated forms. The level of phytoestrogens in total soybeans and their bioavailability are relatively high, and their metabolism is similar to that of endogenous sex hormones. A diet rich in soybeans may affect estrogen metabolism. See Adlercruetz, H. et al, J. Steroid. Biochem., 24: pp 289 to 296 (1986).

Phytoestrogens and their metabolites interact with specific cell receptors and compete with endogenous hormone molecules [see Folman, Y. et al, J. Endocr., 44:213 to 218 (1969)], but the biological estrogen-like effect of these compounds is relatively weak. See Kaziro, R. et al, J. Endocr., 103:395 to 399 (1984) and Tang, B. Y. et al, J. Endocr. 85:291 to 297 (1980).

Phytoestrogens can induce two different effects in an organism. When the level of endogenous sex hormones is relatively high, the antiestrogenic effect prevails. There are several mechanisms of antiestrogenic activity of phytoestrogens, including feedback inhibition at the hypothalamus and pituitary glands, and competition and blockade of cell receptors. It has been observed that a phytoestrogen- and lignan-rich diet is associated with the reduction of free plasma estradiol, and the risk of breast cancer. See Adlercreutz, H. et al, J. Steroid. Biochem., 27:1135 to 1144 (1987) and Mousavi, Y. et al, Steroids, 58:301 to 304 (1993). On the other hand in postmenopausal women, phytoestrogens can provoke an estrogenic response. See Adlercruetz, H. et al, Lancet, 339:1233 (1992). This dual effect of weak estrogens is perceptible, and well known "partial" antigens such as Tamoxifen have these properties.

OBJECT OF THE INVENTION

The object of the invention is to provide a composition based on soybeans that will inhibit the pathogenic processes of osteoporosis by decreasing bone resorption and delaying the onset of clinical manifestations of the disease in elderly patients, especially postmenopausal women.

SUMMARY OF THE INVENTION

I have found that the following new compositions are highly effective in the prevention of the onset of clinical manifestations of osteoporosis in mammalian subjects, especially postmenopausal females suffering from estrogen deficiency. The compositions contain the following active ingredients expressed in parts by weight, such as milligrams:

(a) 75 to 200 parts of one or more phytoestrogen compounds;
(b) 0 to 100 parts of dried licorice root extract;
(c) 300 to 600 parts of calcium contained in a biologically acceptable calcium salt;
(d) 70 to 280 parts of magnesium contained in a biologically acceptable magnesium salt;
(e) 4 to 25 parts of zinc contained in a biologically acceptable zinc salt;
(f) 5 to 20 parts of beta-carotene;
(g) 0.005 to 0.010 parts of Vitamin D as cholecalciferol; and
(h) 6 to 12 parts of Vitamin E.

The new compositions may also include a non-toxic inert carrier or diluent in admixture with the abovementioned active ingredients. Examples of such non-toxic, inert carriers include wheat starch, and sodium carboxymethyl cellulose.

The amount of phytoestrogens (e.g. isoflavones) administered per day may be 200 mg which is a preferred daily dosage of the abovementioned compositions corresponds to the amount of isoflavones naturally occurring in 50–75 g of raw soybeans. This is the average amount of soybeans consumed daily in an Oriental diet. 200 mg of isoflavones are functionally equivalent to the daily dosage of conjugated steroidal estrogen used in hormone replacement therapy.

The weak estrogenecity of soybean phytoestrogens and their metabolites is beneficial for saving bone mass, and for prevention of osteoporosis and fractures.

The licorice root extract contains biologically active compounds, including water-soluble B complex vitamins, triterpenoids, and flavonoids. The licorice root extract has an estrogen-like hormonal effect, and stimulates interferon production. These properties are beneficial for enhancing bone formation by the osteoblasts.

Including a pharmaceutically acceptable calcium salt in the compositions is one of the most effective ways to facilitate the treatment and prevention of osteoporosis. The daily calcium intake necessary for obtaining a net absorbed calcium in excess of the urinary and dermal calcium losses, and which thereby ensure skeletal integrity, is generally about 1,370 mg for an individual weighing about 70 kg. Controlled clinical trials have shown that in postmenopausal women, bone loss is attenuated by increased calcium intake (more than 1000 mg/day). For prevention and treatment of osteoporosis in symptom-free individuals, the goal of calcium supplementation is to achieve a total daily intake of 2500 mg. While any pharmaceutically acceptable calcium salt may be employed for this purpose, the preferred calcium salt is calcium carbonate.

I wish to point out, however, that in order for the calcium to be successfully absorbed and assimilated a cooperative action is needed between the calcium, other minerals, and vitamins, specifically, magnesium, manganese, zinc, iron, phosphorus, Vitamin A, Vitamin C and Vitamin D.

One of the effects that results from the lack of estrogen during menopause is a deficiency in magnesium. Increasing the subject's intake of magnesium in the form of a pharmaceutically acceptable magnesium salt is an effective approach to deceleration of bone loss. A preferred magnesium salt for this purpose is magnesium oxide.

Zinc is especially important for calcium uptake, protein synthesis, and collagen formation (the organic matrix of bone). Sufficient intake and absorption of zinc is needed to maintain the proper concentrations of Vitamin E in the blood. Daily zinc dosages under 100 mg in a patient weighing about 70 kg enhance the immune response, but daily zinc dosages above that level may actually depress the immune system.

Vitamin A is essential for cell growth and differentiation. The preferred source of Vitamin A is the naturally occurring beta-carotene from fruits and vegetables. A preferred unit dosage of the abovementioned composition contains up to 20 mg. The principal reasons why beta-carotene is the preferred form of the Vitamin A are as follows:

carotenoids, unlike Vitamin A, have unique antioxidant properties, and can trap free radicals such as nascent oxygen; thus the antioxidant properties will retard bone resorption; and even though the average adult in the United States consumes the RDA level of Vitamin A, less than one-third of the Vitamin A is in the form of plant carotenoids.

Vitamin E is another essential ingredient in the compositions. Vitamin E is an antioxidant that prevents cell damage by inhibiting free radical formation. Besides this property, Vitamin E induces production of transforming growth factor beta by human cells. This factor is a strong inhibitor of bone resorption.

Vitamin D is required for calcium and phosphorus absorption and utilization, bone formation and normal remodeling. It is important in the treatment and prevention of osteoporosis. Dietary Vitamin D supplementation in the form of cholecalciferol is not toxic so long as it does not exceed 150 mcg/day.

There are two classes of phytoestrogens that are especially contemplated to be within the scope of the present invention. Those two classes are the isoflavones and the coumestans. Examples of the isoflavones include daidzein, genistein, glycitein, and their glycosides: daidzin, genistin, and glycitin, as well as acetylated forms of the abovementioned compounds. An example of a coumestan is coumestrol.

The new compositions according to the invention may contain any one or several phytoestrogens in combination. A preferred combination of the phytoestrogens includes: daidzin 120 to 180 parts by weight, genistin 280 to 350 parts by weight, daidzein 80 to 120 parts by weight and genistein 8 to 12 parts by weight. As a possible variant, the combination can include daidzin and genistin in equimolar concentrations, and 11–13% as aglycones.

When the abovementioned compositions are administered to a mammalian subject as a pharmaceutical, they are preferably administered orally in a dose of 6 to 20 mg of active ingredients per kg of body weight. By active ingredients, I do not mean only the phytoestrogens, but the other ingredients mentioned in the compositions as well. The optimum dosage of course depends on the body weight of the subject as well as the severity of the osteoporosis. Such a daily dosage of the compositions will give the subject the needed volume of calcium and phytoestrogen necessary to improve hormonal status and to save bone mass as well as prevent fractures.

When the mammalian subject is a human, the new pharmaceutical compositions are preferably administered as tablets or capsules 3 or 4 times a day, each containing 150 to 400 mg of the total active ingredients or 50 to 70 mg of the phytoestrogens.

The new compositions may also be employed as dietary supplements for mammalian subjects. When the new compositions are employed as dietary supplements, they are preferably orally administered as tablets or capsules. When the mammalian subject is a human, once again the same daily intake of 3 to 4 tablets or capsules, each containing 150 mg to 400 mg of active ingredients is preferred.

There are no restrictions on age and duration for using the new compositions as pharmaceuticals or dietary supplements for preventing osteoporosis. Generally, these compositions will be administered to postmenopausal women who are at least 50 to 55 years of age and who suffer from an estrogen deficiency. It is noted, however, that a reduction in total bone mass often begins before the female patient reaches menopause. Thus the compositions may be given to females who have not as yet reached menopause who already show symptoms of osteoporosis.

When the new compositions are employed as dietary supplements, they may be admixed with the mammalian subject's food rather than given as individual compositions in tablet or capsule form. Dietary wafers and liquid supplements which contain all of the active ingredients of the dietary supplement in unit dosage form are especially contemplated.

I would also like to point out that a soybean diet, and hence the presently claimed compositions, are not contraindicated in males. Osteoporosis effects elderly men also, and the influence of preventative compounds can be helpful.

Through osteoporosis treatment by hormone replacement therapy using the new compositions of the present invention, I have found that soybean dietary intervention can facilitate the conservation of bone mass, or even increase bone density in one or more skeletal areas in as little as 3 to 6 months. It will decrease the risk of fractures in the future, and this decrease will be considerable. The alleviation of bone pain and improvement in biochemical markers will be more quickly apparent in only one month's time.

In perspective, on the basis of developing and assessing the use of a soybean diet for prevention of osteoporosis, it is possible to design special food products for elderly people. Indeed nutritional requirements, especially vitamin requirements, are different for middle age and older adults. The USA RDA recommends higher levels of some vitamins and minerals. Natural dietary phytoestrogens can replace estrogen therapy. The presently disclosed compositions which contain phytoestrogens have the ability to improve hormonal balance, and are highly effective in the treatment of osteoporosis in older women and men, especially women postmenopause.

The following examples are preferred features of the invention:

EXAMPLE 1

The following composition is prepared in the form of a tablet:

| | | |
|---|---|---|
| (1) | soybean isoflavone (phytoestrogens) genistin | 75 mg |
| (2) | licorice root extract (dried) | 50 mg |
| (3) | calcium carbonate | 750 mg |
| (4) | magnesium oxide | 160 mg |
| (5) | zinc sulfate | 15 mg |
| (6) | beta-carotene | 5 mg |
| (7) | Vitamin D (cholecalciferol) | 5 mcg |
| (8) | Vitamin E (natural RRR α-tocopherol) | 6 mg | with the balance a pharmaceutically acceptable inert carrier.

EXAMPLE 2

The following composition is identical with that of Example 1 except that the 75 mg of genistin is replaced by the 75 mg of the following mixture of phytoestrogens:

| | |
|---|---|
| daidzin | 160 parts |
| genistin | 315 parts |
| daidzein | 97 parts |
| genistein | 9.9 parts. |

EXAMPLE 3

The following composition is prepared in the form of a capsule:

| | |
|---|---|
| soybean coumestrin (phytoestrogen) coumestrol | 50 mg |
| calcium carbonate | 300 mg |
| magnesium oxide | 160 mg |
| zinc sulfate | 25 mg |
| beta-carotene | 20 mg |
| Vitamin D (as cholecalciferol) | 5 mcg |
| Vitamin E (natural RRR α-tocopherol) | 12 mg |

All contained in a non-toxic gelatin capsule.

What is claimed is:

1. A composition for the treatment or prevention of osteoporosis which comprises:
   (a) 75 to 200 parts of one or more phytoestrogen compounds, wherein the phytoestrogen compound is a coumestan or an isoflavone selected from the group consisting of daidzein, genistein, glycitein, daidzin, genistin, glycitin, an acetylated form thereof and mixtures thereof;
   (b) 0 to 100 parts of dried licorice root extract;
   (c) 300 to 600 parts of calcium contained in a biologically acceptable calcium salt;
   (d) 70 to 280 parts of magnesium contained in a biologically acceptable magnesium salt;
   (e) 4 to 25 parts of zinc contained in a biologically acceptable zinc salt;
   (f) 5 to 20 parts of beta-carotene;
   (g) 0.005 to 0.010 parts of Vitamin D as cholecalciferol; and
   (h) 6 to 12 parts of Vitamin E, in admixture with a biologically acceptable inert carrier.

2. The composition for the treatment or prevention of osteoporosis defined in claim 1 wherein the phytoestrogen compound is a coumestan.

3. The composition for the treatment or prevention of osteoporosis defined in claim 1 wherein the mixture of isoflavones includes:

120 to 180 parts by weight of daidzin;
280 to 350 parts of genistin;
80 to 120 parts by weight of daidzein; and
8 to 12 parts by weight of genistein.

4. The composition for the treatment or prevention of osteoporosis defined in claim 2 wherein the coumestan is coumestrol.

5. A method of treating or preventing osteoporosis in a mammalian subject which comprises the step of administering to said subject an amount of the composition defined in claim 1 effective to treat or to prevent osteoporosis.

6. The method of treating or preventing osteoporosis defined in claim 5 wherein the composition is orally administered to the mammalian subject.

7. The method of treating or preventing osteoporosis defined in claim 5 wherein the mammalian subject to which the composition is administered is a postmenopausal female subject.

8. The method of treating or preventing osteoporosis defined in claim 6 wherein the composition is a dietary supplement administered to the mammalian subject as a tablet or capsule.

9. The method of treating or preventing osteoporosis defined in claim 6 wherein the composition is a dietary supplement admixed with the subject's food.

10. A composition for the treatment or prevention of osteoporosis which comprises:

(a) 75 parts by weight of genistin;
(b) 50 parts by weight of dried licorice root extract;
(c) 750 parts by weight of calcium carbonate;
(d) 160 parts by weight of magnesium oxide;
(e) 15 parts by weight of zinc sulfate;
(f) 5 parts by weight of beta-carotene;
(g) 0.005 parts by weight of Vitamin D as cholecalciferol; and
(h) 6 parts by weight of Vitamin E; in combination with a biologically acceptable inert carrier.

* * * * *